United States Patent [19]

Ishizuka

[11] Patent Number: 5,143,075
[45] Date of Patent: Sep. 1, 1992

[54] ULTRASONOGRAPHIC APPARATUS FOR DIAGNOSIS

[75] Inventor: Yoshizo Ishizuka, Fuji, Japan

[73] Assignee: Terumo Kabushiki Kaisha, Tokyo, Japan

[21] Appl. No.: 427,084

[22] PCT Filed: Apr. 8, 1988

[86] PCT No.: PCT/JP88/00357
§ 371 Date: Oct. 6, 1989
§ 102(e) Date: Oct. 6, 1989

[87] PCT Pub. No.: WO88/07838
PCT Pub. Date: Oct. 20, 1988

[30] Foreign Application Priority Data

Apr. 8, 1987 [JP] Japan .................................. 62-84595

[51] Int. Cl.[5] .................................. A61B 8/00
[52] U.S. Cl. .................................. 128/661.01; 73/626
[58] Field of Search .................. 128/661.01; 73/625, 73/626

[56] References Cited

U.S. PATENT DOCUMENTS 4,174,705 11/1979 Buchner ...................... 128/661.01
4,841,491 6/1989 Kondo et al. .............. 128/661.01 X
4,926,872 5/1990 Broch-Fisher et al. ........ 128/661.01
4,962,667 10/1990 Ogawa et al. .............. 128/661.01 X

FOREIGN PATENT DOCUMENTS 2472753 12/1979 France .
261443 8/1984 Japan .

OTHER PUBLICATIONS

Halliwell, Michael, IEE Proceedings, vol. 134, No. 2, 1987 "Ultrasonic imaging in medical diagnosis", pp. 179-187.

Primary Examiner—Francis Jaworski
Attorney, Agent, or Firm—Staas & Halsey

[57] ABSTRACT

An ultrasonographic apparatus for diagnosis which produces a sectional image of an object by a shifting focus system or a variable aperture system from echoes which are obtained from ultrasonic waves radiated to the object. The echoes from the object are transformed into echo signals based on their intensity (100, 102). The echo signals are individually delayed by different periods of time to form signals associated with different depths of the object (110, 112). Among the delayed echo signals, those associated with a particular depth are combined (108, 113A, 113B, 114A, 114B, 116A, 116B, 118A, 118B, 120, 122A, 122B, 124) with the result that a sectional echo image of the object is displayed (126, 128, 130). In the event of changing the depth or the aperture, the level of the echo signal (204) coming out of an adder (120) is adjusted by an amount of delay which is set in a delay circuit (116A, 116B), whereby the average level of the composed echo signal (204) upon the change of the depth of the aperture is maintained substantially equal to an ordinary level. Hence, the influence of a change in sensitivity ascribable to a shift of focus or a changeover of aperture is minimized and, yet, a high resolution is achieved in the lateral direction.

13 Claims, 6 Drawing Sheets

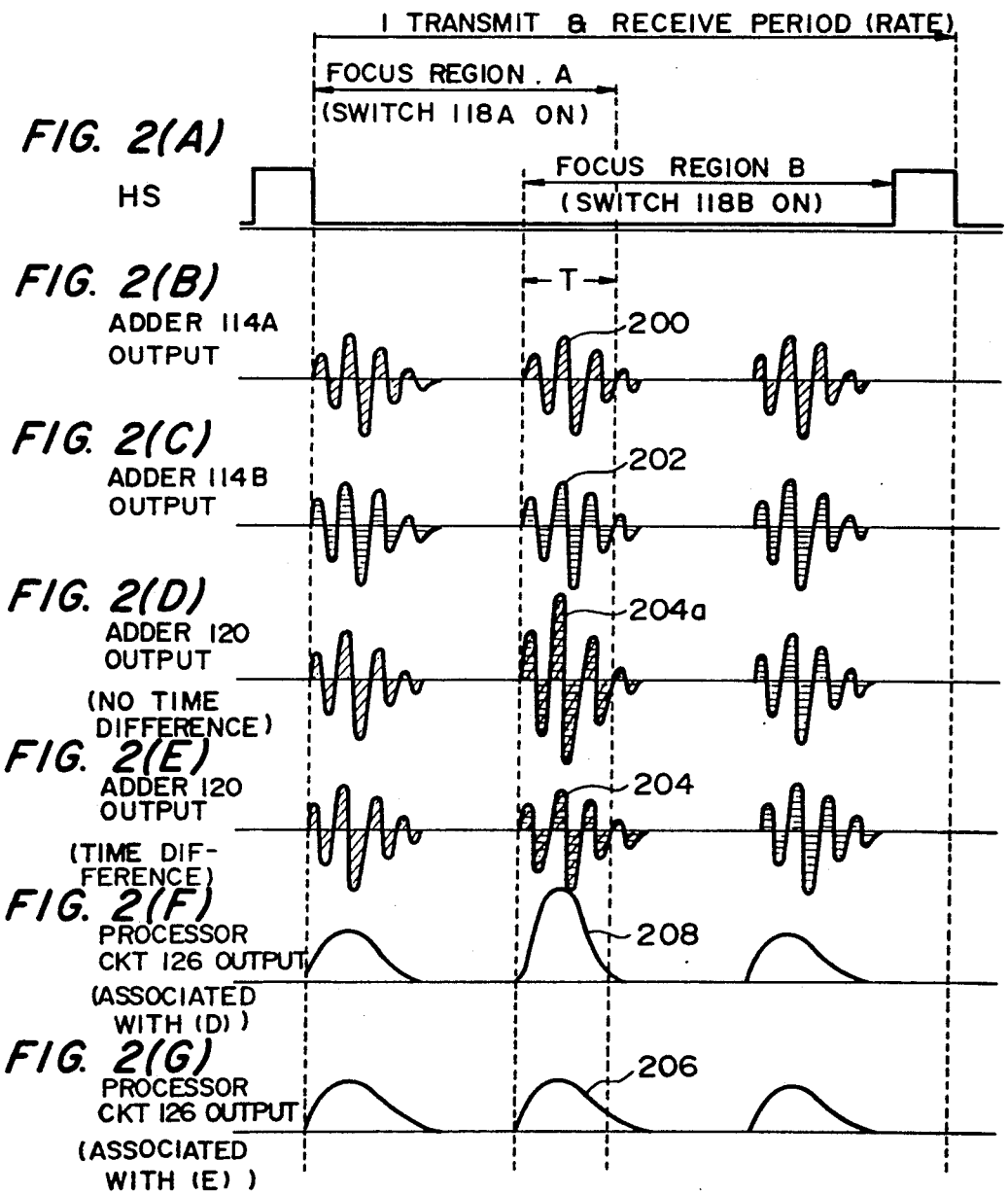

ULTRASONOGRAPHIC APPARATUS FOR DIAGNOSIS

BACKGROUND OF THE INVENTION

1. Field of the Invention

The present invention relates to an ultrasonographic apparatus for diagnosis and, more particularly, to a shifting focus type and/or variable aperture type ultrasonographic apparatus for diagnosis.

2. Description of the Related Art

A diagnostic ultrasonographic apparatus is generally constructed and arranged such that an ultrasonic wave is focused at various predetermined depths of an object such as a human body, thereby enhancing the resolution of an ultrasonic echo image in the lateral direction. A linear array electronic scanning type diagnostic ultrasonographic apparatus, for example, includes a plurality of ultrasonic transducers which are arranged in a linear configuration. It is a common practice with this type of apparatus to achieve a focus effect electronically by delaying transmit wave signals adapted to drive a plurality of ultrasonic transducers relative to each other in one transmission and reception time, i.e., at one rate for transmitting and receiving an ultrasonic wave in the form of a single pulse, the transducers each being associated with a different channel. Another approach to achieve such an electronic focus effect known in the art is delaying received wave signals which are outputted in association with echoes incident to the individual ultrasonic transducers from an object relative to each other and then combining the delayed signals. More specifically, both the two approaches hitherto employed give relative phase differences to transmit wave signals or received echo signals.

The electronic focus system stated above is advantageous in that the focus can be changed rapidly by electronic control and therefore shifted to a plurality of depths on a real time basis. On the other hand, a shifting focus system which shifts the focus in one reception period suffers from two different problems as follows. First, when the taps of delay devices which are adapted to apply different delays to the transducers channels are changed over by switches, an all OFF state causes a dark line to appear at a corresponding point of an image even though the duration of the all OFF state may be short. Conversely, an all ON state (overlap) causes a bright line to appear. Second, even if both of the all OFF state and the all ON state are eliminated, i.e., even if an arrangement is so made as to hold either one of the switches associated with the different regions in an ON state without fail, a difference in picture quality before and after the changeover sharply appears because the ultrasonic acoustic field is different between nearby focus ranges. In this manner, there is a fear that a portion where the changeover has occurred is clearly visible in an output image.

As exemplarily shown in FIG. 4, assume that the focus is shifted from a focus region A defined at a depth of 30 millimeters of an object to a focus region B defined at a depth of 60 millimeters. Then, in a portion where the focus regions A and B overlap each other due to the shift of the focus, the sensitivity is changed to produce a light or a dark strip 12 in an output image. Such a bright line and a light (or dark) strip prevent an output image from appearing even and smooth. This is particularly critical when it comes to diagnosis of the kind deciding normalcy/abnormalcy of a human body by observing delicate changes in the intensity of echoes in the affected part. It is therefore necessary to minimize the influence of a change in sensitivity in the event of a shift of the focus.

To compensate for the change in sensitivity, the switches may be replaced with variable resistor elements which allow the transition from an ON state to an OFF state and vice versa to proceed little by little. This scheme, however, needs an extra implementation for uniformizing the rates of resistance changes in the two focus regions because the variable resistor elements each being associated with a respective one of the focus regions are not exactly the same with respect to characteristics. Such an implementation not only complicates the construction of a control circuit but also needs extra production stages for the selection of elements and adjustment.

The problem discussed above has also been encountered with a variable aperture type ultrasonographic apparatus for diagnosis which receives a reflection from an object while sequentially increasing its effective ultrasound receiving area with the depth. Specifically, when a sectional image of an object received through a comparatively narrow aperture by intermediate transducers of an ultrasonic transducer array and a sectional image received through a comparatively wide aperture by all of the transducers of the array are switched to each other, the sectional image appearing on a video monitor suffers from a discontinuous area between the two regions.

SUMMARY OF THE INVENTION

It is therefore an object of the present invention to eliminate the drawbacks particular to the prior art as discussed above and provide an ultrasonographic apparatus for diagnosis which minimizes the influence of a change in sensitivity ascribable to a shift of focus or a change in aperture and, yet, achieves a high resolution in the lateral direction.

In accordance with the present invention, an ultrasonographic apparatus for diagnosis for radiating ultrasonic waves toward a desired object and producing a sectional image of the object by a shifting focus type system from echoes which are returned from the object comprises wave receiving circuit means comprising a plurality of electroacoustic transducers to which the echoes from the object are incident, the wave receiving means outputting a plurality of first signals which have been delayed by delay times each being different from the others in association with intensity of the echoes and with a plurality of depths defined in the object, and selective signal combining means for producing a second signal by selectively combining the plurality of first signals which are associated with particular one of the depths. The wave receiving circuit means delays relative to one of the plurality of first signals another first signal which follows the one first signal by a predetermined period of time. This predetermined period of time is selected such that the second signal holds a substantially same average level before and after the selective signal combining means changes selection of the plurality of first signals.

In a preferred embodiment of the present invention, the electroacoustic transducers receive echoes from the object and output echo signals associated with the intensity of the echoes. The wave receiving circuit means produces the plurality of first signals by delaying the echo signals which are outputted by the electroacoustic transducers by the periods of time which are different from each other.

In a specific embodiment of the present invention, the wave receiving circuit means comprises a plurality of first adding means individually associated with the plurality of first signals for adding the first signals which are associated with at least a part of the electroacoustic transducers, and a plurality of delay means individually associated with the first adding means for delaying outputs of the first delaying means while maintaining the delay times. The selective signal combining means comprises selecting means for selecting outputs of the delay means one at a time, and second adding means for adding the output selected by the selecting means.

In another specific embodiment of the present invention, the wave receiving circuit means comprises delay means connected to the electroacoustic transducers for producing the plurality of first signals by delaying received signals from the electroacoustic transducers by the delay times. The delay means delays relative to one of the plurality of first signals another first signal which follows the one first signal by a predetermined period of time. The selective signal combining means comprises a plurality of first adding means for individually adding, among the first signals delayed by the delay means, the first signals which are associated with at least a part of the electroacoustic transducers, selecting means for selecting outputs of the plurality of first adding means one at a time, and second adding means for adding the outputs selected by the selecting means.

Further, in accordance with the present invention, an ultrasonographic apparatus for diagnosis for radiating an ultrasonic wave toward a desired object and producing a sectional image of the object by a variable aperture type system from echoes which are returned from the object comprises wave receiving circuit means comprising a plurality of electroacoustic transducers to which the echoes from the object are incident and outputting a plurality of first signals which are associated with the intensity of the echoes, and selective signal combining means for producing a second signal by selectively combining, among the plurality of first signals, the first signals which are associated with a plurality of apertures in the object. The wave receiving circuit means delaying relative to one of the plurality of first signals another first signal which follows the one first signal by a predetermined period of time. This predetermined period of time is selected such that the second signal holds a substantially same average level before and after the selective signal combining means changes selection of the plurality of first signals.

In accordance with the present invention, when the focus is shifted, an echo signal from the following focus is provided with a phase difference relative to an echo signal from a preceding focus. This is also true when the aperture of received acoustic wave is variable. Consequently, the composed waveform of the two echo signals has an average level which is substantially equal to the average level of the non-combined signals.

BRIEF DESCRIPTION OF DRAWINGS

FIG. 2 shows the waveforms of signals which appear in various portions of the ultrasonographic apparatus shown in FIG. 1 in distinction from a prior art system;

DESCRIPTION OF THE PREFERRED EMBODIMENTS

Preferred embodiments of the ultrasonographic apparatus for diagnosis in accordance with the present invention will hereinafter be described in detail with reference to the accompanying drawings.

Figure 1:
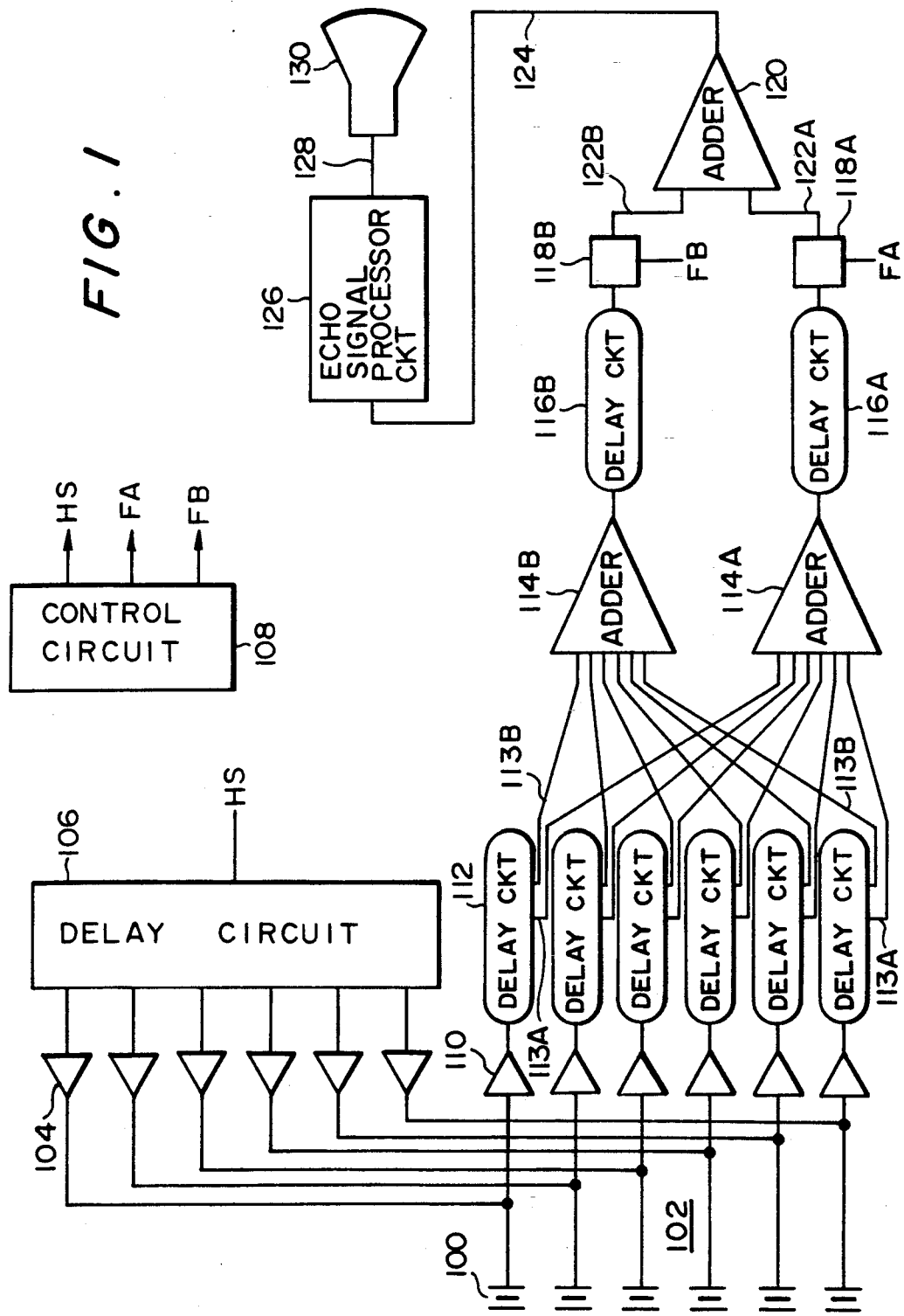
FIG. 1 is a schematic block diagram showing an ultrasonographic apparatus for diagnosis embodying the present invention which is implemented by the shifting focus system.

Referring to FIG. 1, an ultrasonographic apparatus embodying the present invention is shown and implemented by the previously discussed shifting focus principle. As shown, the apparatus includes a plurality of, six in the illustrative embodiment, ultrasonic transducers 100 which are arranged in a linear or concentric configuration to constitute a transducer array 102. The transducers 100 each serves as an electroacoustic transducer for transforming an electric signal or transmit signal applied thereto into an ultrasonic wave and transforming an ultrasonic wave which it receives into an electric signal or received signal. The linear or concentric transducer array 102 is laid on the surface of an object such as a human body and plays the role of a probe for radiating and receiving ultrasonic waves by electrical or mechanical scanning on the basis of the shifting focus type system, i.e. dynamic focus type system.

A transmitting section which forms a part of the diagnostic apparatus of FIG. 1 is constructed as follows. The transmitting section includes a delay circuit 106 and transmit amplifiers 104 the inputs of which are connected to the delay circuit 106. The ultrasonic transducers 100 are each connected to the output of a respective one of the transmit amplifiers 104. A control circuit 108 delivers a control signal HS to the delay circuit 106. In response, the delay circuit 106 delays by a predetermined period of time drive signals, or transmit wave signals, which are to be individually fed to the transducers 100. Consequently, ultrasonic pulses to be transmitted from the individual transducers 100 are shifted in phase relative to each other by predetermined values. In the illustrative embodiment, the transducers 100 defining six independent channels are individually driven by transmit wave signals each having a different phase, and those transducers 100 of intermediate channels are delayed more than those which are close to opposite ends of the array 102. Due to such phase differences, an ultrasonic wave issuing from the transducer array 102 is focused at a predetermined depth.

In a receiving section which forms the other part of the ultrasonographic apparatus shown in FIG. 1, the ultrasonic transducers 100 are each connected to a respective one of delay circuits 112 via an exclusive preamplifier 110. The ultrasonic pulses emitted from the ultrasonic transducers 100 are reflected by different portions of an object and then received by the transducers 100 in the form of ultrasonic echoes. In response, the transducers 100 individually produce electric signals, or echo signals, which are associated with the incoming ultrasonic echoes. Each of the delay circuits 112 delays the echo signal coming out of its associated ultrasonic transducer 100 by a period of time which is associated with a predetermined focus region. Hence, outputs of the delay circuits 112 are coincident with each other with respect to phase on a focus-by-focus basis.

More specifically, the delay circuits 112 are so constructed and arranged as to delay the echo signals coming out of those transducers 100 which are located in the central part of the transducer array 102 more than the echo signals coming out of the other or peripheral transducers 100, the signals being different in phase from each other. In the illustrative embodiment, each delay circuit 112 is provided with two taps 113A and 113B as shown in the figure. As regards the delay times of peripheral portions relative to the central portion, the taps 113B produce signals which have been delayed by a small amount while the taps 113A produce signals which have been delayed by a large amount. Stated another way, the delay circuits 112 are constructed such that the taps 113A and 113B focus respectively at a short distance and at a long distance as measured from the surface of the transducer array.

The outputs 113A and 113B of each delay circuit 112 are coupled to adders 114A and 114B, respectively. The adder 114A serves as a signal combining circuit for adding the outputs 113A of the delay circuits 112. Likewise, the adder 114B plays the role of a signal combining circuit for adding the outputs 113B of the delay circuits 112. Since the delay circuits 112 produce echo signals which are coincident with each other with respect to phase as stated earlier, they are converted by the adders 114A and 114B into a substantially single echo signal. Stated another way, the delay circuits 112 are individually loaded with delay times which allow the outputs of the adders 114A and 114B to have substantially a single waveform. Due to such phase differences or time lags, the ultrasonic echoes received by the transducer array 102 from a predetermined depth of an object, i.e., a depth associated with the amount of delay of the taps 113A or 113B are focused. The depth at which ultrasonic echoes are focused are generally referred to as a focus region or sometimes as a channel. In this particular embodiment, two different focus regions are available in the depthwise direction.

While the delay circuits 112 have been shown and described as comprising two taps 113A and 113B each, they may be provided with three or more taps for the purpose of enhancing the resolution in the lateral direction over a wider range of depths. In the illustrative embodiment, although the echo signals from all of the transducers 100 in the array 102 are picked up through the two groups of taps 113A and 113B, this is not restrictive and only illustrative. Specifically, the circuitry may be modified such that echo signals from a part of the transducer array 102 are picked up with certain delays relative to the others.

The outputs of the adders 114A and 114B are connected to delay circuits 116A and 116B, respectively. These delay circuits 116A and 116B have delay times which are different from each other. The difference between such delay times, i.e., phase difference $\phi$ will be described in detail later.

The delay circuit 116A is connected to one input terminal 112A of an adder 120 by way of a switching circuit 118A. Likewise, the delay circuit 116B is connected to the other input terminal 112B of the adder 120 via a switching circuit 118B. Adding the signals coming in through the input terminals 112A and 112B, the adder 120 produces a composed waveform of the input signals. The control circuit 108 delivers control signals FA and FB to the switching circuits 118A and 118B, respectively. Opened and closed under the control of the signals FA and FB, the switching circuits 118A and 118B selectively apply the output signals of their associated delay circuits 116A and 116B to the inputs 122A and 122B of the adder 120. In this configuration, the switching circuits 118A and 118B and the adder 120 constitute a selective signal combining circuit in cooperation.

The output 124 of the adder 120 is connected to an echo signal processing circuit 126 whose output 128 is in turn connected to a cathode ray tube or similar video monitor 130. The echo signal processing circuit 126 applies to an output signal of the adder 120 various kinds of signal processing such as luminance intensification and luminance modulation which are suitable for displaying the signal on the video monitor 130. The video monitor 130 therefore displays an echo image of the object which is represented by the ultrasonic echoes received by the transducer array 102.

Adapted to control the operations of the entire ultrasonographic apparatus, the control circuit 108 delivers the control signal HS to the delay circuit 106 for controlling the drive of the ultrasonic transducers 100 and the switching signals FA and FB for controlling the switching circuits 118A and 118B, in response to manually entered commands by way of example.

When the control circuit 108 applies the control signal HS to the delay circuit 106, the delay circuit 106 delays a transmit signal by predetermined delay times so that ultrasonic pulses which will focus to a particular region are emitted from the ultrasonic transducers 100.

Ultrasonic echoes returned from a particular portion of an object are incident to the ultrasonic transducers 100 and converted thereby into echo signals. Then, each delay circuit 112 produces via its tap 113A an echo signal delayed by a period of time which is associated with a certain focus region A such as a 30 millimeters deep focus region as measured from the surface of the object and via the tap 113B an echo signal delayed by a period of time which is associated with the other focus region B such as a 60 millimeters deep focus region. The signals on the taps 113A and signals on the taps 113B are applied to the adders 114A and 114B, respectively.

Each of the adders 114A and 114B adds the outputs of their associated taps of the six delay circuits 112 to produce a single echo signal. The echo signals from the adders 114A and 114B are fed to their associated delay circuits 116A and 116B and thereby delayed by predetermined amounts.

When it is desired to display the echo image associated with the focus region A on the video monitor 130, the control circuit 108 activates the control signal FA for closing the switch circuit 118A while deactiving the control signal FB for opening the switching circuit 118B. In this condition, the echo signal from the delay circuit 116A is fed to the input terminal 122A of the adder 120 while no signal is applied to the other input terminal 122B. As a result, only the echo signal picked up through the taps 113A of the delay circuits 112 and delayed by the delay circuit 116A in association with the focus region A appears on the output 124 of the adder 120 and is applied to the echo signal processing circuit 126. This signal is displayed on the video monitor 130 after being modulated with respect to luminance as one rate of echo image by the processing circuit 126.

On the other hand, when it is desired to display the echo image associated with the focus region B on the video monitor 130, the control circuit 108 activates the switch circuit 118B instead of the switch circuit 118A within a certain one rate period. Such a changeover is effected by closing the switching circuit 118B and then opening the switching circuit 118A, as shown in FIG. 2(A). More specifically, as shown in FIGS. 2(B) and 2(C), both of the switching circuits 118A and 118B are kept closed only for a duration of T in which the echo signal representative of echoes from the focus region A, i.e., a received signal 200 (FIG. 2(B)) applied from the taps 113A of the delay circuits 112 to the switch circuit 118A via the adder 114A and delay circuit 116A and the echo signal representative of echoes from the other focus region B, i.e., an echo signal 202 (FIG. 2(C)) applied from the taps 113B to the switch circuit 118B via the adder 114B and delay circuit 116B overlap each other.

Figure 3A:
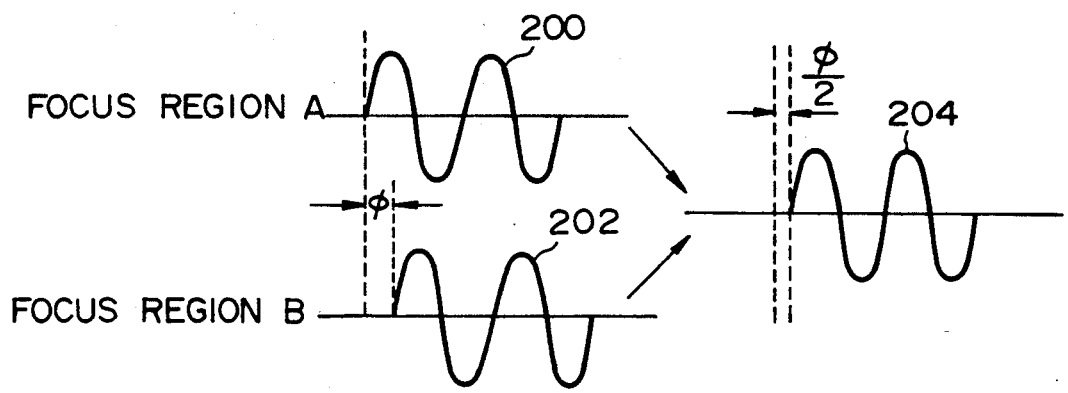
FIG. 3A shows signal waveforms useful for understanding the principle of the present invention.

The delay times of the delay circuits 116A and 116B are selected such that the two echo signals 200 and 202 overlap each other over their major portions during the period of time T and, when they are respectively applied to the input terminals 122A and 122B of the adder 120 via the switch circuits 118A and 118B, the adder 120 produces on its output 124 a composed echo signal 204 (FIG. 2(E)) whose amplitude level is substantially the same as that of the original received signals 200 and 202. Such delay times will be better understood with reference to FIG. 3A. In FIG. 3A, a phase difference or time lag $\phi$ exists between the delay times of the delay circuits 116A and 116B and is predetermined such that an output signal 204 of the adder 120 to which the echo signals 200 and 202 are fed has an average amplitude level equal to that of the original signals 200 and 204. The delay times of the delay circuits 116A and 116B are so selected as to produce such a time lag $\phi$.

Assuming that the echo signals 200 and 202 have the same amplitude of $V_o$ and that the phase difference $\theta$ between the signals 200 and 202 is $2\pi T/\tau$, then by the addition theorem of trigonometric function there holds an equation:

$$v_o = V_o \sin\omega t + V_o \sin(\omega t + \theta)$$
$$= 2V_o \cos(-\theta/2) \cdot \sin(\omega t + \theta/2)$$

where T is equal to 1/f, f is the ultrasonic frequency, and $\tau$ is the delay time. By selecting the phase difference $\theta$ such that $\cos(-\theta/2) = \frac{1}{2}$ holds, there is produced an equation:

$$V_o = V_o \sin(wt + \theta/2)$$

It will be seen from the above that the amplitude level is not changed despite the addition.

More specifically, as shown in FIGS. 3A and 2(E), the echo signal 204 appearing on the output 124 of the adder 120 when the switch circuits 118A and 118B are operated to switch the focus range A to the focus range B has an average output level which is substantially the same as that of a usual or echo signal which appears when such a changeover is not effected. So long as the composed signal 204 has such an average level, the composed video signals are subjected to luminance modulation at substantially the same signal level by the echo signal processing circuit 126 (FIG. 2(G), 206). It follows that the echo image appearing on the video monitor 130 is free from a bright line and a light or a dark strip (FIG. 4) otherwise developed upon the change of the focus range as has been discussed in relation to the prior art.

Figure 5:
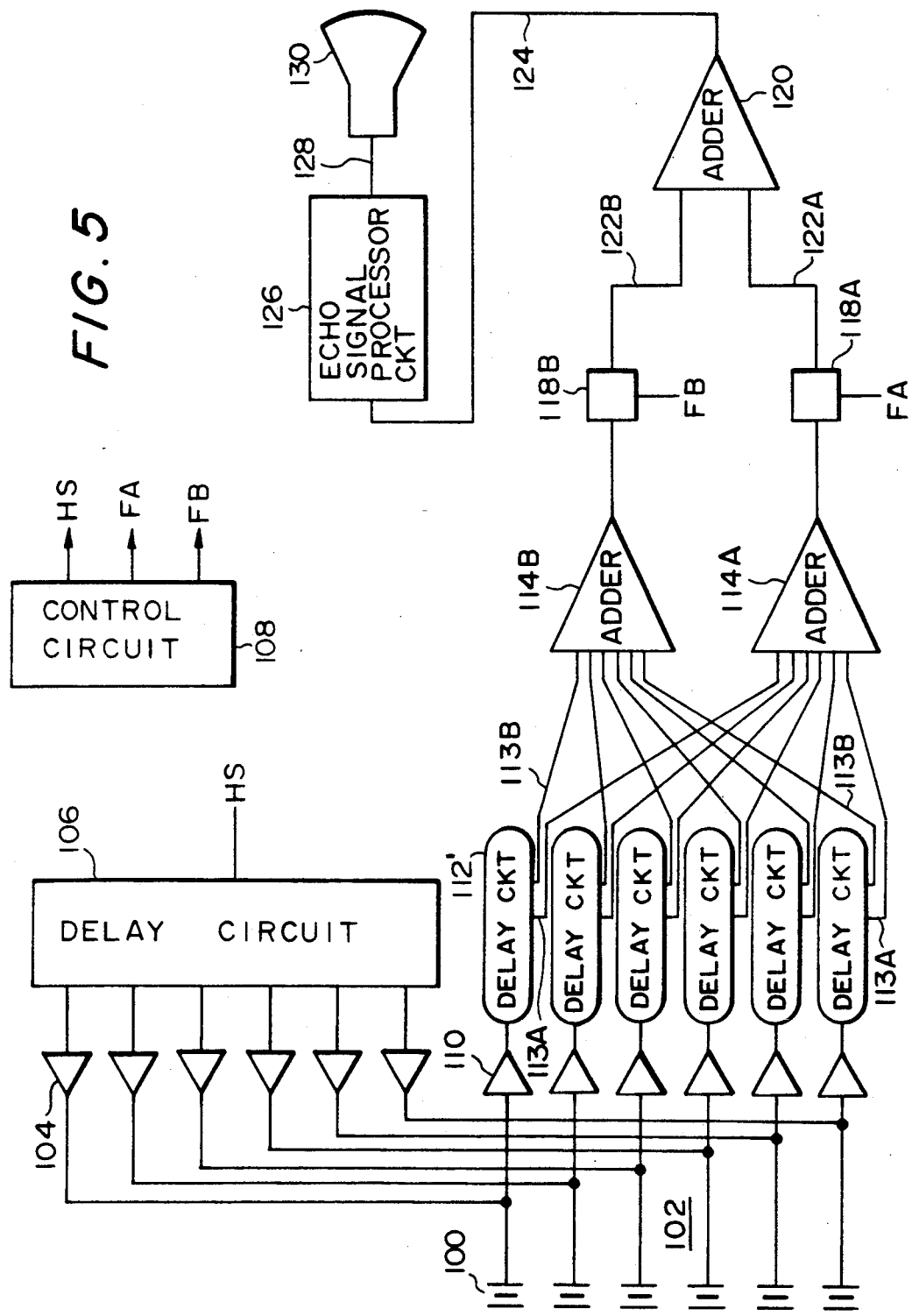
FIG. 5 is a view similar to FIG. 1, showing an alternative embodiment of the diagnostic apparatus in accordance with the present invention.

In the illustrative embodiment, the delay circuits 116A and 116B adapted to implement the time lag between the echo signals which are individually associated with two different focus ranges are connected between the adder 114A and the switch circuit 118A and between the adder 114B and the switch circuit 118B, respectively. Alternatively, as shown in FIG. 5, each delay circuit 112 itself may be constructed to produce such a time lag between the echo signal appearing on the tap 113A and the echo signal appearing on the tap 113B.

Thereafter, the control circuit 108 opens the switch circuit 118A and holds the switch circuit 118B in a closed state. Then, only the echo signals appearing on the taps 113B of the delay circuits 112 and delayed in association with the focus range B are routed through the adder 114B, delay circuit 116B and switch circuit 118B to the adder 120. These signals are eventually visualized on the video monitor 130. The procedure described above is repeated to sequentially scan the object in a direction which is parallel to the surface of the object, whereby a complete sectional image of the object is provided on the screen of the video monitor 130.

Figure 3B:
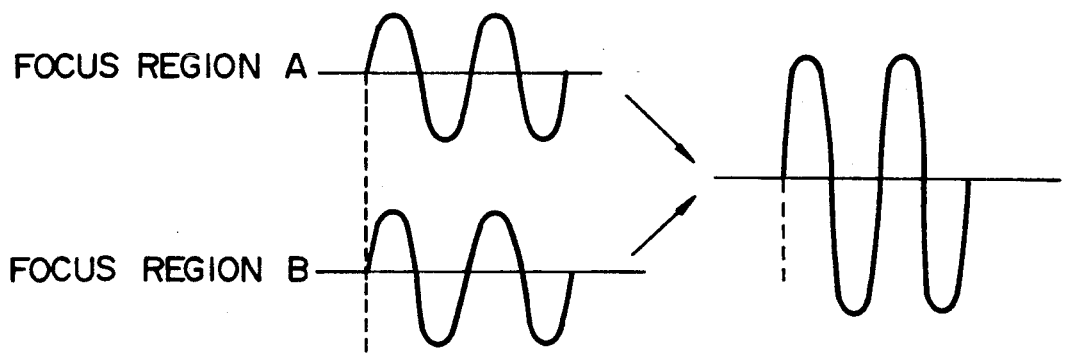
FIG. 3B is a diagram similar to FIG. 3A, showing a prior art system.

Assume that the delays assigned to the delay circuits 116A and 116B are so selected as not to provide the phase difference or time lag $\phi$. Then, as shown in FIGS. 3B, 2(D) and 2(F), a received signal 204a (FIG. 2D) produced on the output 124 of the adder 120 upon the change of the focus range from A to B has a higher output level than the usual output level. In such a condition, the composed signal 204 coming out of the adder 120 would undergo luminance modulation at a different signal level from the usual signal level 208 (FIG. 2(F) at the echo signal processing circuit 126 with the result that a bright line and/or a light or dark strip 12 would be developed in the echo image on the video monitor 130.

As stated above, in the illustrative embodiment, the level of the composite echo signal 204 from the adder 120 is adjusted by the delays assigned to the delay circuits 116A and 116B in the event that the focus range is switched from one to the other. This allows the composed echo signal 204 to have substantially the same average level as the usual level despite the changeover of the focus range. Such an achievement is derived from the fact that an echo signal has an AC waveform and its frequency remains substantially constant.

Figure 6:
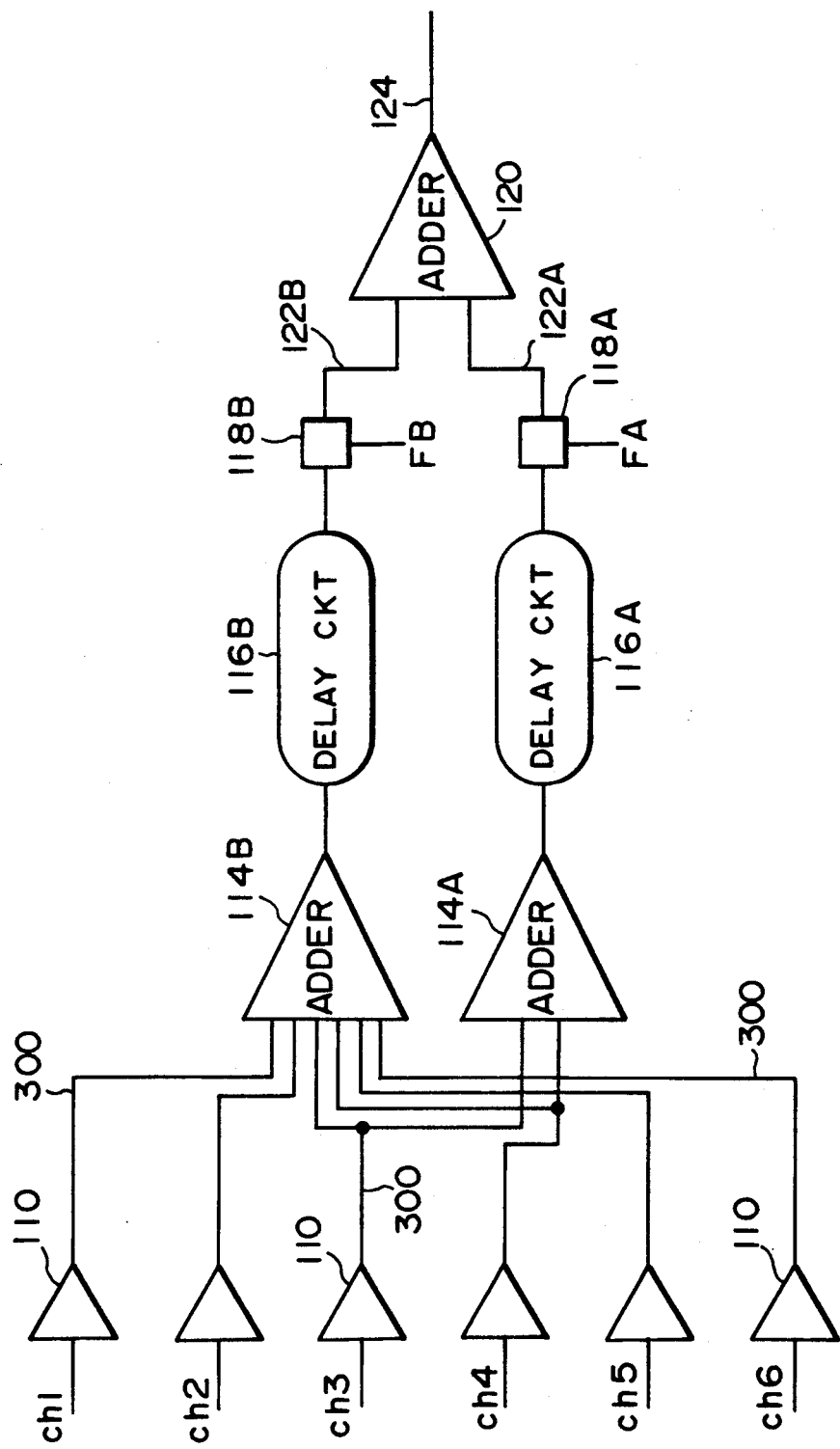
FIG. 6 is a view similar to FIG. 1, showing another alternative embodiment of the diagnostic apparatus in accordance with the present invention which is implemented by the variable apperture type system.

While the present invention has been shown and described in relation to a shifting focus type ultrasonographic apparatus for diagnosis, it is similarly applicable even to a or dynamic aperture type ultrasonographic apparatus which receives a wave by sequentially increasing an aperture or effective acoustic wave receiving area with the depth and has heretofore suffered from a discontinuous section of an object. A part of an alternative embodiment of the present invention applied to a variable aperture type ultrasonic apparatus is shown in FIG. 6. The circuitry shown in FIG. 6 is a substitute for the circuitry which intervenes between the transducer array 102 and the echo signal processing circuit 126 of FIG. 1. In this particular embodiment, the transducer array 102 is operated with the variable aperture principle.

Figure 4:
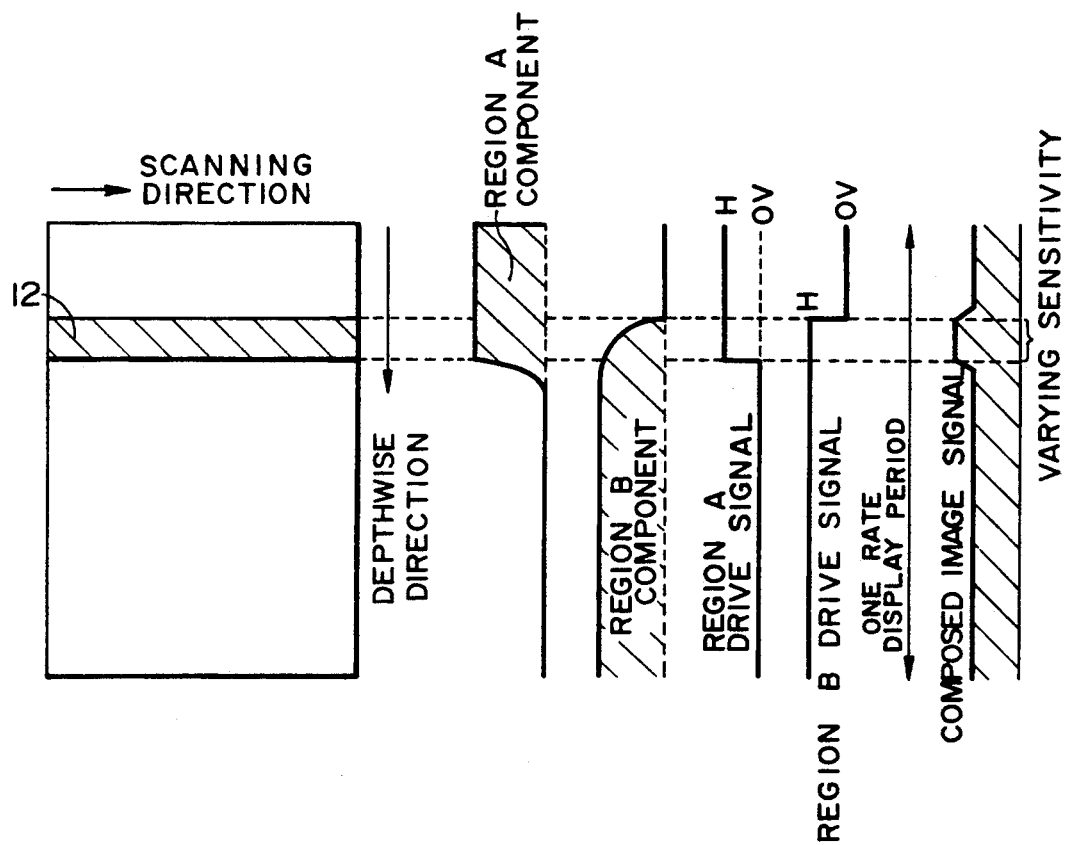
FIG. 4 is a diagram schematically showing an example of ultrasonic echo images which may be displayed by the prior art system.

In FIG. 6, the six transducers 100 individually define channels (ch) #1 to #6 of the whole aperture for receiving a reflection from an object. The outputs 300 of all the amplifiers 110 individually associated with the channels #1 to #6 are connected to the inputs of one adder 114B. Further, the outputs 300 of those amplifiers 110 which are located on the intermediate channels 3 and 4 are further connected to the inputs of the other adder 114B, as illustrated. The gains of the adders 114A and 114B are adjusted in matching relation to the variable aperture of the transducer array 102 so as to prevent a substantial difference of sensitivity from occurring between the two display image regions A and B to be displayed (FIG. 4). The delay circuits 116A and 116B, switch circuits 118A and 118B and adder 120 of this alternative embodiment may be the same as those of the embodiment shown in FIGS. 1 to 5. The switching circuits 118A and 118B are individually controlled by the controls signals FA and FB from the control circuit 108 to select one of a comparatively narrow aperture which is defined by the channels 3 and 4 only and a comparatively wide aperture which is defined by all of the channels 1 to 6.

With the above arrangement, the circuitry shown in FIG. 6 achieves excellent directivity for both of the regions which are close to and remote from the electroacoustic transducers 100 while substantially eliminating discontinuous variations in sensitivity between the display regions A and B. The variable aperture type diagnostic apparatus may be combined with the previously stated shifting focus type diagnostic apparatus to further enhance the resolution in the lateral direction. Such a combination may be implemented by connecting the output taps 113A of only those delay circuits 112 of FIG. 1 which are associated with the intermediate two or four channels of the transducer array 102 to the inputs of the adders 114A and by increasing the gain of the adder 114A accordingly.

The present invention is applicable to an ultrasonographic apparatus for diagnosis and especially to a shifting focus type or a variable aperture type ultrasonographic diagnostic apparatus. In accordance with the present invention, when the focus of the apparatus is shifted, an echo signal returned from a new focus region is provided with a phase difference relative to an echo wave returned from an old focus range so that the average level of a composed waveform of the two different kinds of echo signals is substantially the same as that of the original signals. In the case of a variable aperture type apparatus, when the aperture is changed, an echo signal from a new aperture is provided with a phase difference relative to echo waves from an old aperture. This minimizes the influence of a change in sensitivity which is ascribable to the shift of the focus and thereby realizes excellent resolution in the lateral direction.

I claim:

1. An ultrasonographic apparatus for diagnosis radiating ultrasonic waves toward an object and producing a sectional image of the object by dynamic focusing from echoes which are returned from the object, comprising:

wave receiving circuit means, having a plurality of electroacoustic transducers, for receiving echoes from the object and for producing a plurality of first signals representative of intensities of the echoes, the plurality of first signals being individually delayed by a plurality of delay times different from each other; and selective signal combining means for selectively combining ones of the plurality of first signals which are associated with a particular depth in the object to produce a second signal representative of the combined first signals;

said wave receiving circuit means comprising delay means for delaying relative to one of the plurality of first signals another first signal which follows said one first signal by a predetermined time difference;

said predetermined time difference substantially corresponding to one-third of a period of the plurality of first signals, whereby the second signal holds substantially the same average level before and after said selective signal combining means changes selection of the plurality of first signals.

2. An apparatus in accordance with claim 1, wherein said plurality of electroacoustic transducers receive echoes from the object and outputs echo signals associated with the intensities of the echoes;

the plurality of first signals comprising a plurality of outputs produced by combining the plurality of echo signals by a plurality of delay patterns such that said echo signals converge to a plurality of depths which are different from each other.

3. An apparatus in accordance with claim 2, wherein said delay means comprises:

a plurality of first adding means for providing the plurality of echo signals which are associated with at least a part of said plurality of electroacoustic transducers with time delays in a plurality of delay patterns such that said echo signals converge to a plurality of different depths, and adding the resulting delayed echo signals; and at least one delay means for delaying outputs of said plurality of first adding means while maintaining the predetermined time difference relatively to each other;

said selective signal combining means comprising:

selecting means for selecting an output of said at least one delay means; and second adding means for adding outputs selected by said selecting means.

4. An apparatus in accordance with claim 2, wherein said delay means comprises:

a plurality of first adding means for providing the plurality of echo signals which are associated with at least a part of said plurality of electroacoustic transducers with time delays in a plurality of delay patterns such that said echo signals converge to a plurality of different depths, and adding the resulting delayed echo signals;

said first adding means delaying, when providing the delay patterns, relative to one of the plurality of first signals another first signal which follows said one first signal by the predetermined time difference;

said selective signal combining means comprising:

selecting means for selecting outputs of said first adding means; and second adding means for adding outputs selected by said selecting means.

5. An apparatus as claimed in claim 2, further comprising:

wave transmitting means connected to said plurality of electroacoustic transducers for driving said plurality of electroacoustic transducers by transmit signals each having a different delay time;

whereby said plurality of electroacoustic transducers transmit ultrasonic waves which converge to a part of the object.

6. An apparatus in accordance with claim 5, wherein said electroacoustic transducers are arranged in a one-dimensional array.

7. An apparatus as claimed in claim 1, further comprising image displaying means for displaying the second signal in the form of a sectional echo image by visualizing said second signal.

8. An apparatus in accordance with claim 1, wherein said electroacoustic transducers are arranged in a concentric configuration;

a part of said electroacoustic transducers transmitting and receiving an ultrasonic wave which is delayed by a different period of time relative to at least a part of the remaining electroacoustic transducers to thereby focus the ultrastonic wave at the different depths.

9. An ultrasonographic apparatus for diagnosis radiating ultrasonic waves toward an object and producing a sectional image of the object by a dynamic aperture system from echoes which are returned from the object, comprising:

wave receiving circuit means, having a plurality of electroacoustic transducers, for receiving echoes from the object and for producing a plurality of first signals representative of intensities of the echoes; and selective signal combining means for selectively combining ones of the plurality of first signals which are associated with a plurality of apertures defined in the object to produce a second signal representative of the combined first signals;

said wave receiving circuit means comprising delay means for delaying relative to one of the plurality of first signals another first signal which follows said one first signal by a predetermined period of time;

the predetermined period of time substantially corresponding to one-third of a period of the plurality of first signals, whereby the second signal holds a substantially constant average level through said selective signal combining means changing selection of the plurality of first signals.

10. An apparatus in accordance with claim 9, wherein said delay means comprises:

a plurality of first adding means individually associated with the plurality of first signals for adding the first signals which are associated with at least a part of said electroacoustic transducers; and a plurality of delay means individually associated with said first adding means for delaying outputs of said first delaying means while maintaining the delay times;

said selective signal combining means comprising:

selecting means for selecting outputs of said delay means one at a time; and second adding means for adding the output selected by said selecting means.

11. An ultrasonographic apparatus for diagnosis using echoes of ultrasonic waves radiating toward an object to produce a sectional image of the object by dynamic focusing of the echoes, said ultrasonic apparatus comprising:

wave receiving means, having a plurality of electroacoustic transducers to receive echoes from the object, for producing first and second signals representative of intensities of the echoes from first and second depths, respectively, within the object, the first and second signals being individually delayed by different delay times, said wave receiving means including delay means for delaying the first signals by amounts corresponding to the first depth and the second signals by amounts corresponding to the second depth plus a time delay substantially equal to one-third of the period of the echoes; and selective signal combining means for selectively combining the first and second signals to produce an output signal having a substantially constant average level during switching from combining the first signals to combining the second signals.

12. An ultrasonographic apparatus for diagnosis using echoes, having a period, of ultrasonic waves radiating toward an object to produce a sectional image of the object by dynamic focusing of the echoes, said ultrasonic apparatus comprising:

wave receiving means, having a plurality of electroacoustic transducers to receive echoes from the object, for producing first and second signals representative of intensities of the echoes from first and second depths, respectively, within the object, the first and second signals being individually delayed by different delay times; and selective signal combining means for selectively combining the first and second signals to produce an output signal having a substantially constant average level during switching from combining the first signals to combining the second signals, said selective signal combining means including;

first combining means for combining the first signals to produce a first combined signal;

second combining means for combining the second signals to produce a second combined signal;

delay means for producing first and second delayed signals by delaying the second combined signal substantially one-third of the period of the echoes relative to the first combined signal; and output means for outputting one of the first delayed signal, the second delayed signal and a combined delayed signal produced by adding the first and second delayed signals, as the output signal.

13. An ultrasonographic apparatus for diagnosis using echoes of ultrasonic waves radiating toward an object to produce a sectional image of the object with a dynamic aperture, said ultrasonic apparatus comprising:

wave receiving means, having a plurality of electroacoustic transducers to receive echoes from the object, for producing first and second signals representative of intensities of the echoes using first and second apertures, respectively; and selective signal combining means for selectively combining the first and second signals to produce an output signal having a substantially constant average level during switching from combining the first signals to combining the second signals, said selective signal combining means including
first combining means for combining the first signals to produce a first combined signal;
second combining means for combining the second signals to produce a second combined signal;
delay means for producing first and second delayed signals by delaying the second combined signal substantially one-third of the period of the echoes relative to the first combined signal; and
output means for outputting one of the first delayed signal, the second delayed signal and a combined delayed signal produced by adding the first and second delayed signals, as the output signal.

* * * * *